United States Patent [19]

Crippa

[11] 4,026,433
[45] May 31, 1977

[54] CONTAINER PROVIDED WITH AN OUTER TESTPIECE FOR THE ANALYSIS OF URINE AND OTHER ACID LIQUIDS

[76] Inventor: Egidia Crippa, Via Italia 17, Peregallo di Lesmo, Italy

[22] Filed: Jan. 15, 1976

[21] Appl. No.: 649,185

[30] Foreign Application Priority Data

Jan. 16, 1975 Italy .................................. 19318/75

[52] U.S. Cl. ...................................... 215/6; 4/110; 128/2 F
[51] Int. Cl.² ........................................ B65D 11/02
[58] Field of Search ............... 215/6, 100 R; 4/110; 141/369; 128/2 F, 295

[56] References Cited

UNITED STATES PATENTS

| 787,986 | 4/1905 | Kelliher | 215/6 |
| 895,812 | 8/1908 | Strauss | 215/6 |
| 2,780,225 | 2/1957 | Barr | 215/6 X |
| 3,161,891 | 12/1964 | Bauman | 4/110 |
| 3,635,091 | 1/1972 | Linzer | 128/2 F X |
| 3,830,107 | 8/1974 | Linzer | 128/2 F X |
| 3,859,671 | 1/1975 | Tomasello | 215/6 X |

Primary Examiner—Donald F. Norton
Attorney, Agent, or Firm—William Anthony Drucker

[57] ABSTRACT

Container for analysis, consisting of a container of an approximate frusto-conical shape provided with cover, showing at its side surface a hollow portion, which develops vertically, until almost the edge of the container itself, which is overhanging and connected to a tubular member, projecting on the lower part and serving as a support means for a testpiece.

3 Claims, 5 Drawing Figures

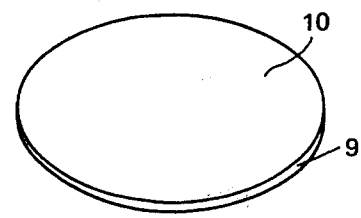
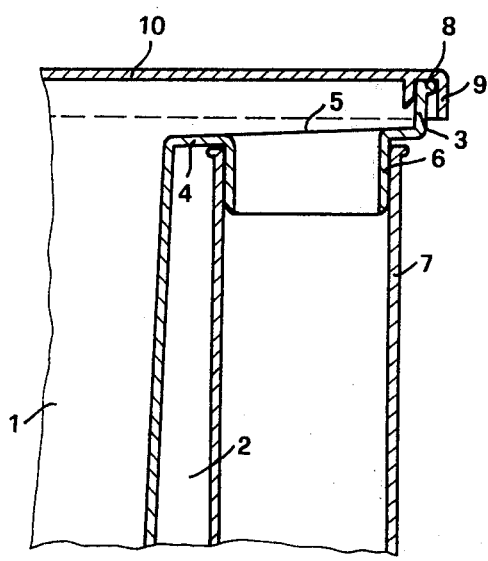
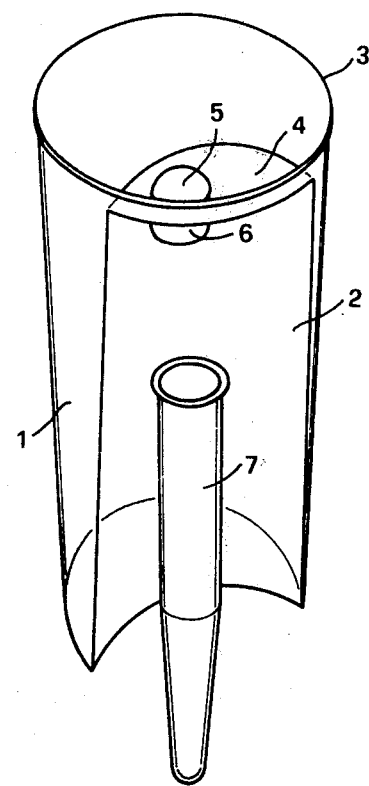

CONTAINER PROVIDED WITH AN OUTER TESTPIECE FOR THE ANALYSIS OF URINE AND OTHER ACID LIQUIDS

This invention relates to a bottle for containing urines and other liquids to be analyzed, being provided with an outer testpiece.

A well known for the analysis of urines, samples of the liquids themselves are generally handed over to the analyst. Such liquid samples are normally collected into generic containers, so that the taking of the said liquids by pouring them off into testpieces shows a series of practical difficulties.

There exist instead specific containers for urines and similar liquids to be submitted to analysis, which include one or more testpieces, which may be filled semi-automatically by suitably operating the containers themselves. The removal of the testpiece therefrom always requires, however, removal of the cover from the containers themselves in order to be in a position of grasping the edge for the testpiece itself.

Consequently, the analyst's hands may come in contact with the liquid, thereby creating the pre-conditions for an alteration thereof and/or possible infective actions. It should likewise be noted that the removal of the testpiece from the container may cause a wetting with urine of the outer portion of the container itself, thereby giving rise to further practical inconveniences. The above-outlined inconveniences are instead obviated by the container for analysis of urines and other liquids according to the present invention.

The container of this invention is in fact provided with a testpiece for taking samples, which is arranged outside the container itself.

More in detail, the container according to the present invention consistsof a glass showing preferably a frusto-conical shape made from suitable transparent plastic material.

The wall of the said glass shows particularly a hollow portion, developing in proximity of the mouth of the glass itself.

The said hollow portion is delimited on the upper portion by a horizontal wall, being approximately elliptic in the middle of which there is drilled a through-hole of suitable diameter, provided with a downwardly turned edge.

Over the said edge there is fitted, obviously from the outside, the mouth of a testpiece being possibly also of a square shape. It should be stated here that the said horizontal wall serving for the upper closing of the convex portion of the glass is placed a conveniently lower height than the edge of the glass itself.

The said edge likewise shows a slight projection to the outside, adapted to anchor the edge of a cover consisting of suitably flexible material. Between the the said cover and the precipitated horizontal wall there is consequently formed a gap through which is is possible to pour off the liquid directly from the glass to the testpiece. The taking of the latter with the liquid sammple is, therefore, effected from the outside without the need for removing the cover from the glass. These and further characteristic features of a functional and constructional nature of the container for urines or other liquids to be analyzed according to this invention could better be understood from the detailed description given below taken in conjunction with the accompanying drawings, in which:

FIG. 4 represents designed the detail of the connection of the testpiece to the glass; and FIG. 5 shows the above container in an exploded perspective view.

Figure 1:
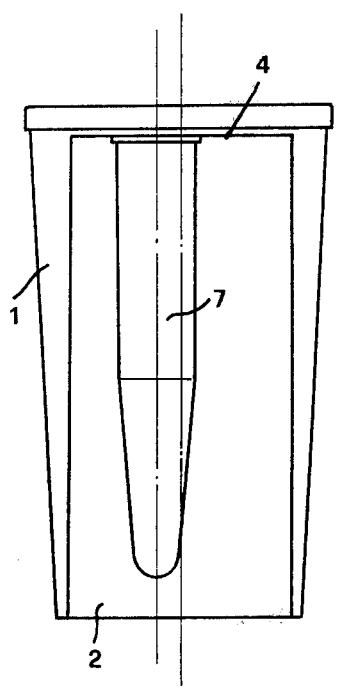
FIG. 1 shows the container of this invention in a front view.
Figure 2:
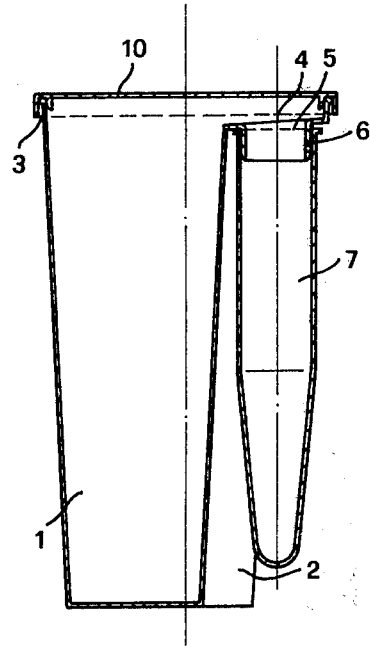
FIG. 2 represents the same container as above, but in a side view.
Figure 3:
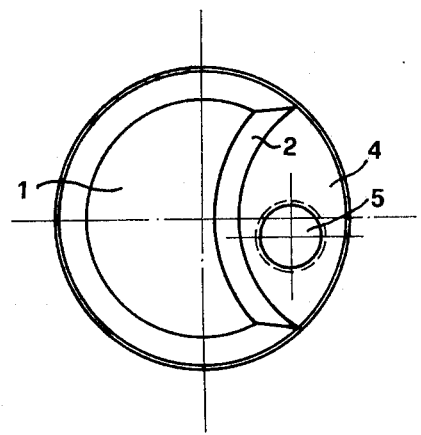
FIG. 3 shows the above container in a view from the bottom.

Referring now particularly to the reference numerals given in the various figures on the accompanying drawings, the container for analysis of this invention consists of a glass 1, made from transparent plastic material, of a preferably frusto-conical shape.

The wall of such glass is provided in particular with a hollow portion 2, which develops vertically until almost the edge 3 of the glass itself. The said hollow portion is closed on the upper part by a horizontal wall 4, showing approximately an ellipitical configuration, which is placed at a lower height than the edge 3 referred to above. In the middle or in another suitable position of such horizontal wall there is drilled a through-hole 5, provided with a support tubular member 6 being turned downwardly.

Over the latter there is fitted the mouth of a testpiece 2 having a section adapted to perform a tight coupling with the edge itself. The edge 3 of the glass 1 shows in turn a peripheral projection 8, which may anchor the edge 9 of a cover 10, obtained from suitably flexible material.

It should be stated that between such cover and the horizontal wall 4 there is formed a gap, adapted to put the glass 1 into communication with the outer testpiece 7.

By such arrangement, it is possible to pour off the liquid contained in the glass from the glass itself to the testpiece, thereby imparting to the container of this invention a convenient inclination.

The removal of the testpiece is likewise effected by operating from the outside the glass 1 without the need for removing the cover thereof. The upper portion of the testpiece 7, fitted externally and laterally to to the body of the glass 1 is connectable to the body of the tubular support member 6, the upper portion of such testpiece 7 showing a diameter being slightly larger than that of the said tubular support member 6 being overlying relative to the testpiece 7 itself.

What we claim is:

1. A container for analysis comprising a container of an approximate frusto-conical shape provided with a cover, a portion of the side wall of the container being recessed along the length thereof until about the upper edge portion of the container, said edge portion overhanging the recessed portion of the side wall, and a tubular member projecting from the lower part of said edge portion and serving as a support for a testpiece.

2. Container for analysis as defined in claim 4, in which the said tubular member is connected to the lower wall of the overhanging portion of the container body so to ensure the pouring off of the liquid to be analyzed from the said container to the said testpiece and vice versa, without removing the closing cover.

3. Container for analysis as defined in claim 1 in which an upper portion of a testpiece includes a mouth which is connected to the tubular member, the mouth of the said testpiece having a slightly larger diameter than the diameter of the said tubular member to closely fit thereover.

* * * * *